(12) United States Patent
Flickinger et al.

(10) Patent No.: US 7,615,079 B2
(45) Date of Patent: Nov. 10, 2009

(54) MONORAIL SYSTEM

(75) Inventors: Eric Flickinger, Atlanta, GA (US); Tom Smithweck, Powder Springs, GA (US)

(73) Assignee: MediTech Advisors, LLC, Atlanta, GA (US)

( * ) Notice: Subject to any disclaimer, the term of this patent is extended or adjusted under 35 U.S.C. 154(b) by 471 days.

(21) Appl. No.: 11/407,585

(22) Filed: Apr. 20, 2006

(65) Prior Publication Data

US 2007/0270873 A1 Nov. 22, 2007

(51) Int. Cl.
*A61F 2/44* (2006.01)
(52) U.S. Cl. .................................. 623/17.16
(58) Field of Classification Search ............. 606/90, 606/107; 623/17.11–17.16
See application file for complete search history.

(56) References Cited

U.S. PATENT DOCUMENTS

| | | | |
|---|---|---|---|
| 5,571,109 A | 11/1996 | Bertagnoli | |
| 5,713,906 A | 2/1998 | Grothues-Spork et al. | |
| 6,110,177 A | 8/2000 | Ebner et al. | |
| 6,267,763 B1 * | 7/2001 | Castro | 606/86 A |
| 6,368,325 B1 * | 4/2002 | McKinley et al. | 606/99 |
| 6,478,800 B1 * | 11/2002 | Fraser et al. | 606/99 |
| 6,491,695 B1 | 12/2002 | Roggenbuck | |
| 6,500,180 B1 | 12/2002 | Foley et al. | |
| 6,824,565 B2 | 11/2004 | Muhanna et al. | |
| 6,855,148 B2 | 2/2005 | Foley et al. | |
| 6,887,248 B2 | 5/2005 | McKinley et al. | |
| 6,929,606 B2 | 8/2005 | Ritland | |
| 6,936,070 B1 | 8/2005 | Muhanna | |
| 6,951,538 B2 | 10/2005 | Ritland | |
| 7,267,690 B2 | 9/2007 | Felt | |
| 2002/0055745 A1 | 5/2002 | McKinley et al. | |
| 2003/0032966 A1 | 2/2003 | Foley et al. | |
| 2004/0073214 A1 | 4/2004 | Mehdizadeh | |
| 2004/0267276 A1 | 12/2004 | Camino | |
| 2005/0154396 A1 | 7/2005 | Foley et al. | |
| 2005/0216088 A1 | 9/2005 | McKinley et al. | |
| 2008/0140206 A1 | 6/2008 | Felt | |

FOREIGN PATENT DOCUMENTS

| | | |
|---|---|---|
| DE | 100 35 182 A | 2/2002 |
| WO | 00/42898 A | 7/2000 |
| WO | 02/062235 A2 | 8/2002 |

* cited by examiner

*Primary Examiner*—Eduardo C Robert
*Assistant Examiner*—Elana B Fisher
(74) *Attorney, Agent, or Firm*—Kilpatrick Stockton LLP; Camilla C. Williams; Wilson L. White (57) ABSTRACT

Systems providing improved methods of performing a spinal fusion procedure and including a monorail instrument that protects the medial neural structures, includes a sliding platform for additional instrumentation and allows controlled delivery of various instruments for disc preparation and implant insertion. The monorail instrument engages other instruments, including various instruments utilized to prepare the disc space as well as spinal fusion implants, for guided and controlled insertion into the disc space. The monorail instrument may be a distractor, and may include flutes for preparation of the disc space.

8 Claims, 13 Drawing Sheets

MONORAIL SYSTEM

FIELD OF THE INVENTION

This invention relates generally to spinal fusion surgery and, in particular, to a system for safely and effectively delivering instruments and an implant during a spinal fusion procedure.

BACKGROUND

The spinal column is a flexible column formed from a linear series of vertebral bones separated by intervertebral discs. These discs reduce friction between adjacent vertebrae and absorb compression forces applied to the spinal column. A vertebra includes an anterior body and a posterior arch that surrounds the spinal cord. Spinal nerves extend from each side of the spinal cord and exit the column at the vertebral foramen, which is formed by the posterior arch. Articular processes, including the superior articular process and the inferior articular process, are small flat projections on the surfaces of the arches.

There are four facet joints associated with each vertebrae, and these joints interlock with adjacent vertebrae. In this manner, facets on the opposing processes determine the range and direction of movement between adjacent vertebrae, hence the flexibility of the spinal column. The facet joints maintain spinal stability, protect the disc from excessive stress, and assist the discs in allowing motion and controlling shear forces. These joints are vulnerable to degenerative spinal disorders.

Degenerative disc disease is typically caused by a loss of disc space height, leading to a narrowing of the neural foramen and subsequent neural compression, and causing back and radicular pain. Instability of the posterior elements can lead to a condition known as spondylolisthesis, in which a vertebral body slips forward in relation to an adjacent vertebrae. This movement of the vertebral body narrows the foramen and results in painful pressure on the nerve roots.

Degenerative disc disease may often be resolved through a spinal fusion procedure using an interbody implant (one which is implanted between the bodies of two adjacent vertebrae). Such interbody implants may be formed from titanium, carbon fiber, allograft, or other suitable material including, but not limited to, biocompatible materials such as PEEK™, available from Invibio®. Implantation of a substitute graft is designed to reestablish normal disc height, provide immediate stability to the motion segment, and provide a matrix for fusion. When the implant grows into the existing bone, the fusion becomes solid and movement is eliminated at that level. A fusion procedure may also involve the surgical implantation of hardware, such as plates, screws or cages.

In order to fuse and thereby stabilize the motion segment, the disc space must be prepared prior to insertion of the interbody device. Soft tissue, such as disc material and cartilage, and other such tissue, is cleaned off the vertebral endplates so that intimate bony contact is obtained between the graft, implant and host tissue. The preparation of the disc space can be achieved with scrapers, curettes, rongeurs, drills, rasps and/or chisels. In preparing the disc space, it is important not to remove too much of the endplate in order to maintain structural integrity so that the interbody implant does not telescope into the vertebral body when normal axial loads are applied.

Posterior Lumbar Interbody Fusion (PLIF) is one surgical fusion technique used to treat degenerative lumbar disc disease. Proper distraction during a PLIF procedure must be achieved in order to gain compression of the implant. Proper distraction allows natural compression across the disc space via the annulus and other posterior elements. This compression delivered to the implant helps stabilize the implant, which avoids expulsion, and keeps the grafting material under stress, thus promoting faster fusion and bone healing.

Transforaminal Lumbar Interbody Fusion (TLIF), also referred to as an extended PLIF, was developed in response to problems associated with PLIF procedures. In the TLIF approach, the disc space is expanded by removing one entire facet joint, while a PLIF is usually performed on both sides of the facet, removing a portion of each of the joints. Removal of the entire facet joint improves visualization into the disc space, allowing removal of more disc material and insertion of a larger implant. Other procedures have been developed to provide anterior column support as well, including the Anterior Lumbar Interbody Fusion (ALIF) and extreme lateral interbody fusion techniques that access the vertebrae through the psoas muscle.

The instruments used in current procedures include design limitations that fail to address the challenges of the neural anatomy or require numerous instruments and steps that add significant time to the surgical procedure. Delivery of an interbody device requires a large amount of bone resection and neural retraction. Removal of the lamina and facet joint, which may be necessary in order to insert the implant, can potentially destabilize the motion segment. In addition, there is increased surgical time due to the more extensive bone removal and disc preparation. Destabilization of the motion segment can interfere with compression of the interbody device, especially in a "stand alone" situation in which additional hardware is not utilized. Therefore, it is necessary to balance the need to deliver an appropriately sized interbody device (to restore the appropriate disc height) without destabilizing the segment (so the necessary compression can occur).

Furthermore, existing methods of introducing interbody implants into the disc space, the freehand method and the controlled method, include disadvantages. First, existing surgical techniques in which an implant is inserted into the disc space freehand (without controlled access) and impacted into proper position present dangers to delicate neural structures. Each time an instrument is introduced or removed from the surgical site, there is a chance that delicate structures, such as the spinal cord or nerve roots, could be compromised, potentially causing severe damage. Additionally, maintaining constant distraction is a challenge, as instruments are passed by the neural structures "freehand." Moreover, if a distractor is placed in the contralateral side of implantation, it does not always address the distraction needs of the operative side.

In existing "controlled" procedures, the instruments used to provide protected access to the disc space often occupy an excessive amount of the disc space. As a result, an implant smaller than that which the disc space is capable of accepting must be used. This smaller implant does not restore proper disc space height and therefore the stability of the fusion is compromised. Furthermore, these instruments require much more bony resection in order to be placed correctly, thus further destabilizing the spine.

In another existing controlled procedure, a series of instruments slide through a channel of a wide profile distractor. This design limits visualization and neural retraction. In addition, the design introduces a significant amount of lateralization to the placement of the implants for PLIF procedures: the implants are spaced farther apart from one another and must be implanted with a significant amount of space between them. Further, this delivery design has poor anatomical fit, as it creates a dead space between the external wall of the retractor and the load bearing surface of the implant.

Thus, there is a need for a system that allows delivery of the appropriate size interbody device (in order to restore disc height), and adequate neural retraction without compromising visualization of the surgical site.

SUMMARY OF THE INVENTION

Systems of this invention provide improved methods of performing a spinal fusion procedure. A monorail instrument according to this invention protects the medial neural structures, provides a sliding platform for additional instrumentation and allows controlled delivery of various instruments for disc preparation and implant insertion. The monorail system of this invention may be adapted for use with each of the PLIF, TLIF, ALIF and extreme lateral (direct lateral) procedures.

One instrument according to this invention includes a monorail on one side, which structure connects to various instruments utilized to prepare the disc space as well as an implant. These instruments and the implant may be designed with a channel corresponding to the monorail, so that the instruments are joined to the monorail instrument for guided and controlled insertion into the disc space. The monorail instrument may be a distractor, and may include flutes for preparation of the disc space.

BRIEF DESCRIPTION OF THE DRAWINGS

FIG. 3 is a lateral view of the distractor of FIG. 1.

FIG. 7 is a side view of a chisel and distractor assembly of this invention.

FIG. 12 is a perspective view of the insertion tool of FIG. 11 and a guide according to this invention.

FIG. 13 is a perspective view of the assembly of an implant, distractor and insertion tool of this invention.

DETAILED DESCRIPTION

One system of this invention provides an improved method of performing a spinal fusion procedure. Generally, the system of this invention includes a tool having a monorail on one side. The instrument includes a monorail on its lateral side that accommodates various instruments utilized to prepare the disc space. For example, additional instruments such as a chisel, rasp and implant may be designed with a channel corresponding to the monorail, so that the instruments are joined to the distractor for guided and controlled insertion into the disc space. In one embodiment, the monorail instrument is a distractor, which may be inserted into the disc space and rotated to properly distract the disc space.

As shown in FIGS. 1-4, the monorail instrument is a distractor 40, which includes a rod 42 having a monorail 44 on its lateral side 46. In the embodiment shown in the drawings, monorail 44 includes flat top portion 48 and angled sides 50, 52 (also shown in FIG. 9). Leading end 54 includes a tapered tip 56 for easier insertion into the disc space. In order to restore the disc height, a surgeon grasps a handle (not shown) attached to trailing end 58 and inserts leading end 54 of distractor 40 into the disc space and then rotates 90 degrees. Shoulder 60 adjacent leading end 54 prevents distractor 40 from over extending into the disc space and damaging spinal tissue. Trailing end 58 of distractor 40 is configured to include a chuck 62 so that it may be joined to a handle, such as a Hudson handle (not shown). Any other suitable handle and handle engagement structure may also be used.

Figure 9:
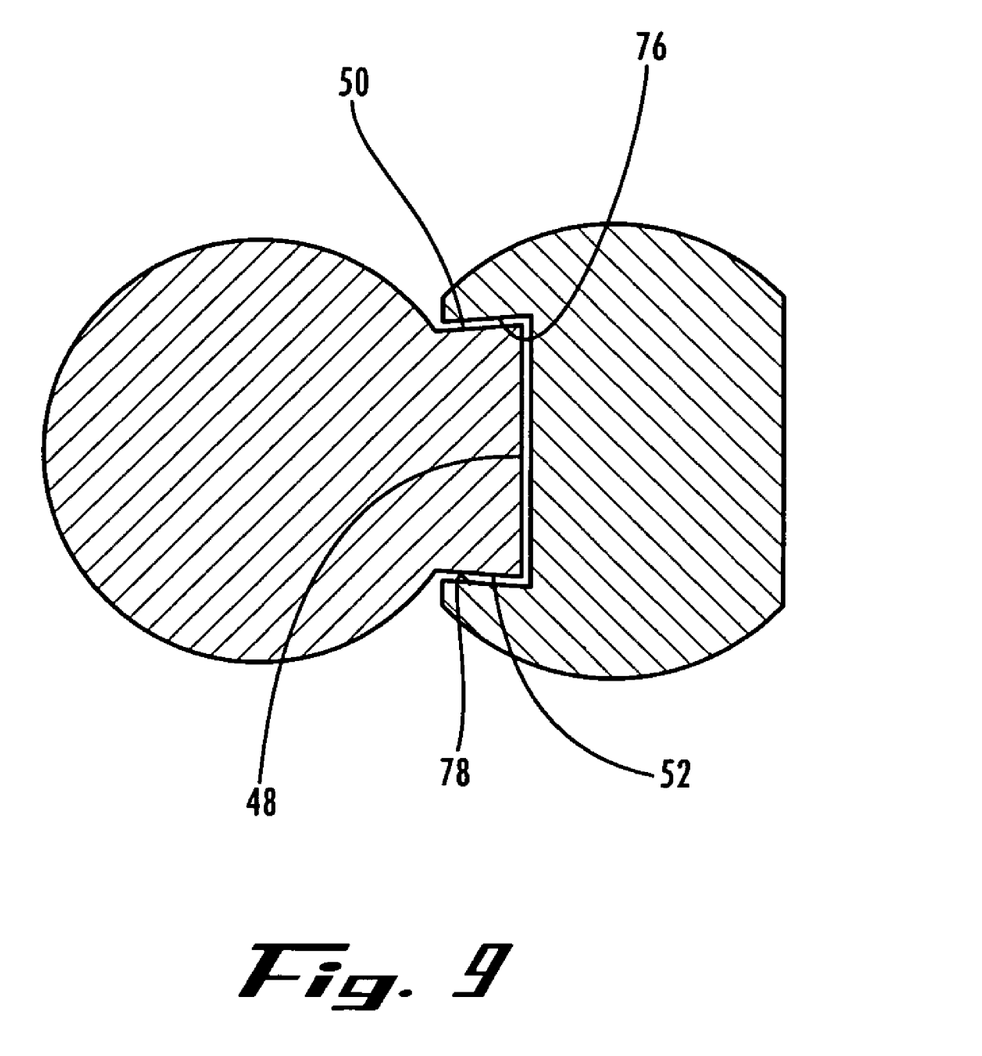
FIG. 9 is an end view in cross section of the chisel and distractor assembly of FIG. 7.

Once the proper distraction is achieved, the distractor 40 remains in the rotated position in the disc space in order to maintain proper distraction. A chisel, rasp, or both, can then used to clean and prepare the disc space for an implant, if desired. As shown in FIGS. 5-9, chisel 70 includes a channel 72, adapted to engage monorail 44 of distractor 40 (FIG. 9). The channel 72 includes a flat bottom surface 74 and slanted sides 76, 78 that correspond to the top portion 48 and sides 50, 52 of the monorail 44. The instruments are joined simply by engaging the leading end 80 of the channel 72 of chisel 70 with narrow section 57 (shown in FIG. 1) at trailing end 58 of the monorail 44. In this manner, channel 72 of chisel 70 engages monorail 44 of distractor 40 so that chisel 70 slides down the rod 42 of distractor 40 and into the disc space. In alternative embodiments, the monorail and channel connection may include alternative structure, such as a rectilinear channel and rail, or any other suitable structure that joins the two instruments and allows controlled access to the disc space.

Figure 1:
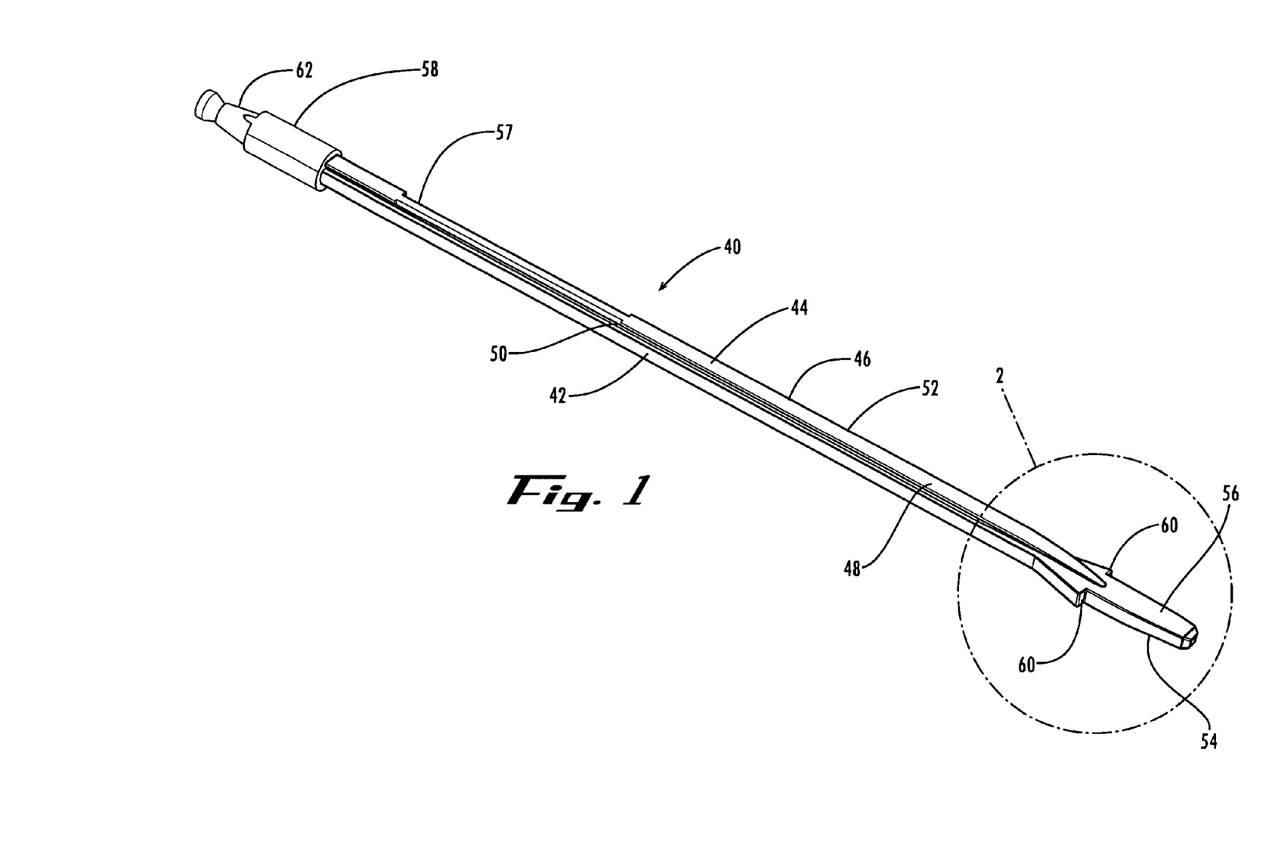
FIG. 1 is a perspective view of a monorail distractor of this invention.
Figure 2:
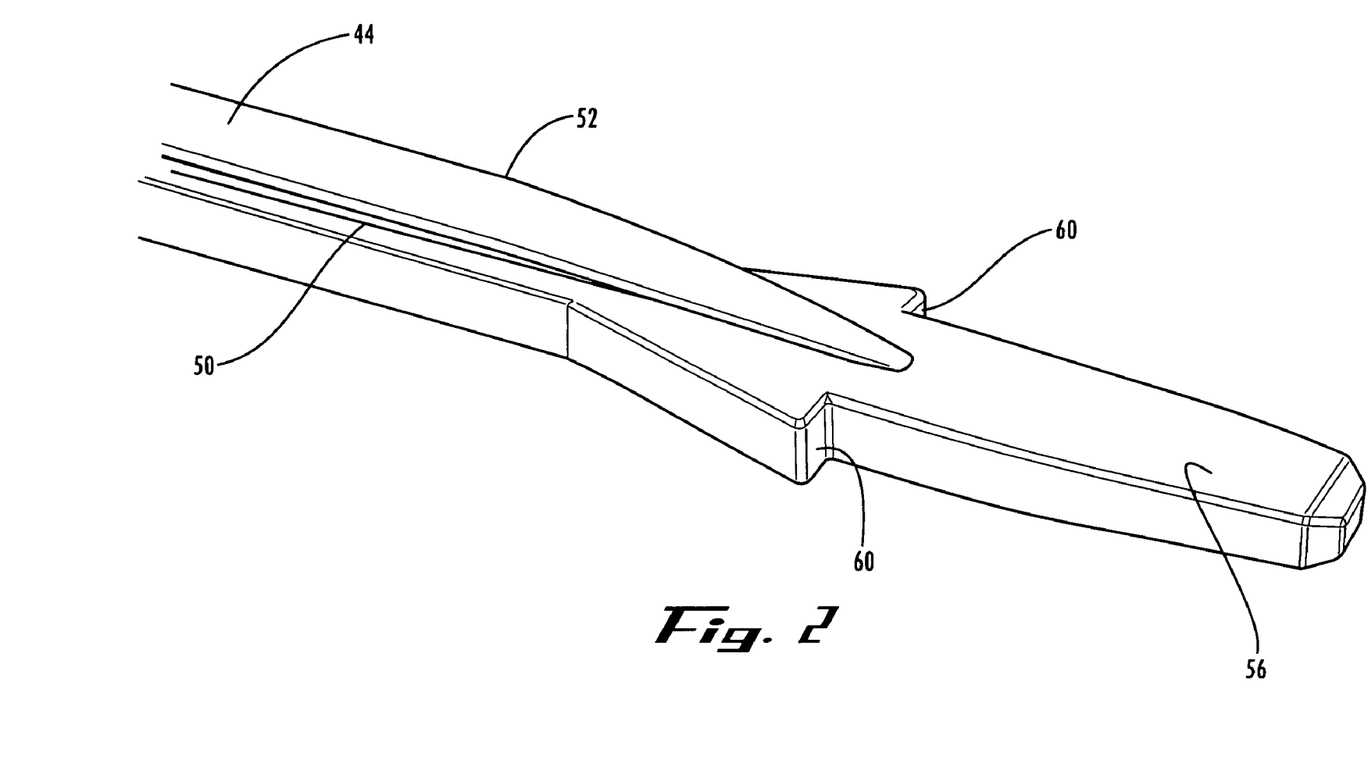
FIG. 2 is an enlarged perspective view of a portion of the distractor of FIG. 1.
Figure 4:
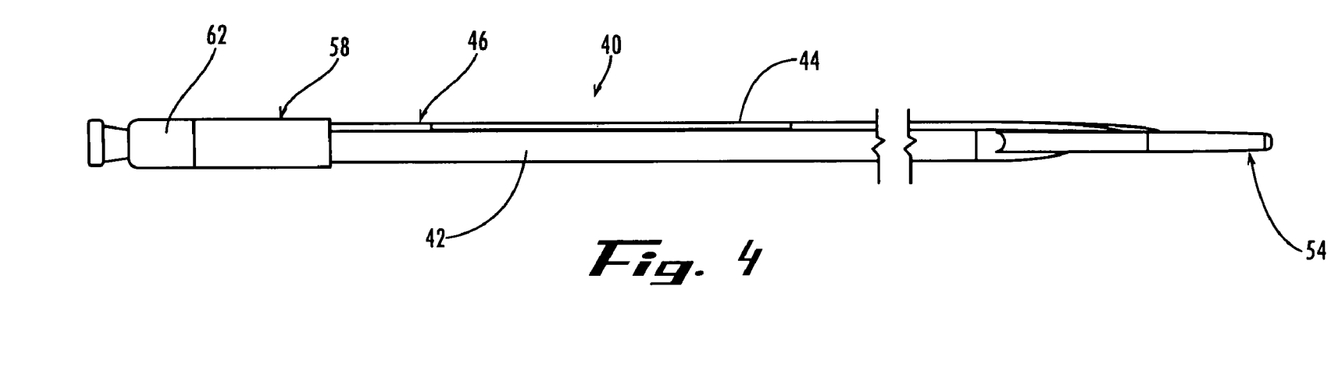
FIG. 4 is a side view of the distractor of FIG. 1.
Figure 5:
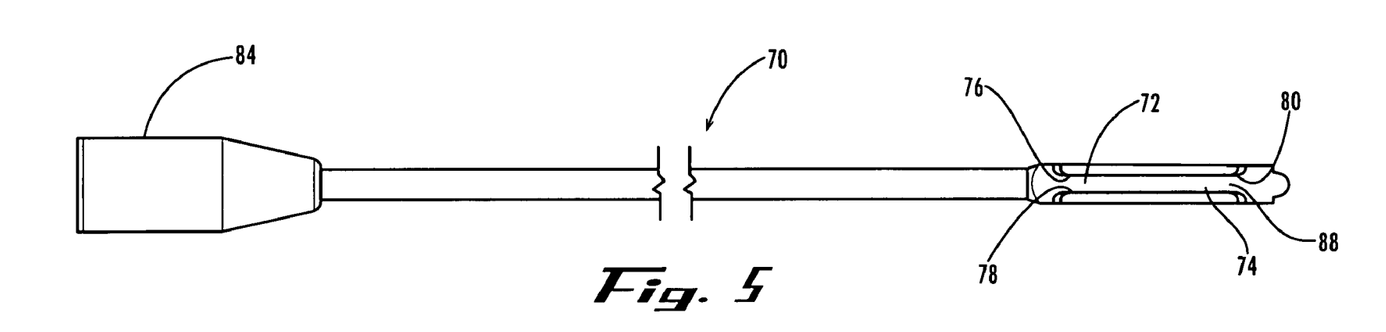
FIG. 5 is a side view of a chisel of this invention.
Figure 6:
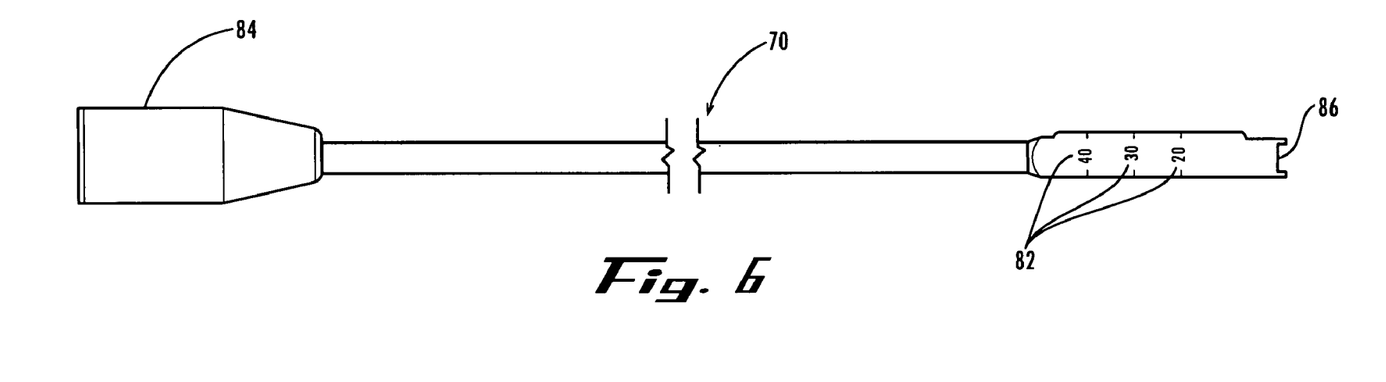
FIG. 6 is a perspective view of the chisel of FIG. 5.
Figure 8:
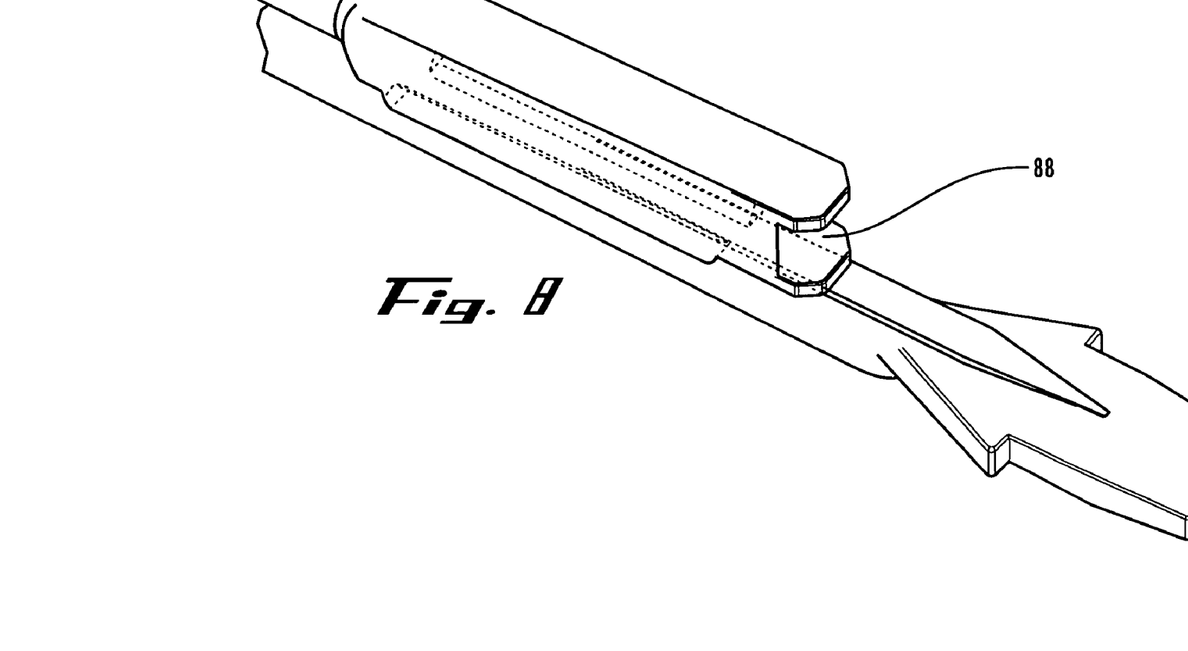
FIG. 8 is a perspective view of a portion of the chisel and distractor assembly of FIG. 7.

As shown in FIG. 5, chisel 70 includes markings 82 or other indicia indicating depth of insertion. In an alternative embodiment, the rod 42 of monorail instrument 40 may include a stop to limit the insertion depth of the chisel into the disc space. The rod 42 shown in the drawings has a rectilinear shape, but any suitable shape, including circular, may be used.

Engagement of the chisel 70 (or other instrument) with the monorail 44 of the distractor 40 thus provides guided delivery and access to the disc space. This controlled access protects the neural elements from potential injury from contact with instruments as they pass by or around the dura, nerve roots and other soft tissue. Once properly engaged with the monorail instrument, the chisel 70 may be impacted using a mallet (not shown) on handle 84 and extracted using a slaphammer (not shown) or any other suitable tool. Cutting end 86 of chisel 70 cuts away tissue, which may be captured in space 88 of chisel 70 and withdrawn from the disc space. A rongeur, or other suitable instrument, may also be used to extract the separated tissue.

In an alternative embodiment, a monorail device may be equipped to prepare the disc space without the use of a chisel or rasp, or in addition to such instrumentation. In this alternative embodiment shown in FIG. 10, the edges 90 of the leading end 92 of the monorail instrument 94 include flutes 96, equipping the monorail device with the ability to cut away soft tissue in the disc space and off the vertebral endplates. In this embodiment, the leading end 92 is inserted into the disc space and turned to distract the space. Turning the instrument 94 causes flutes 96 to cut away tissue. The instrument 94 may be rotated back and forth to remove the tissue. A rongeur may be used to extract the separated tissue. A chisel, rasp, or other appropriate instrument may also be used (as described above) if additional preparation of the disc space is required.

Figures 10, 11:
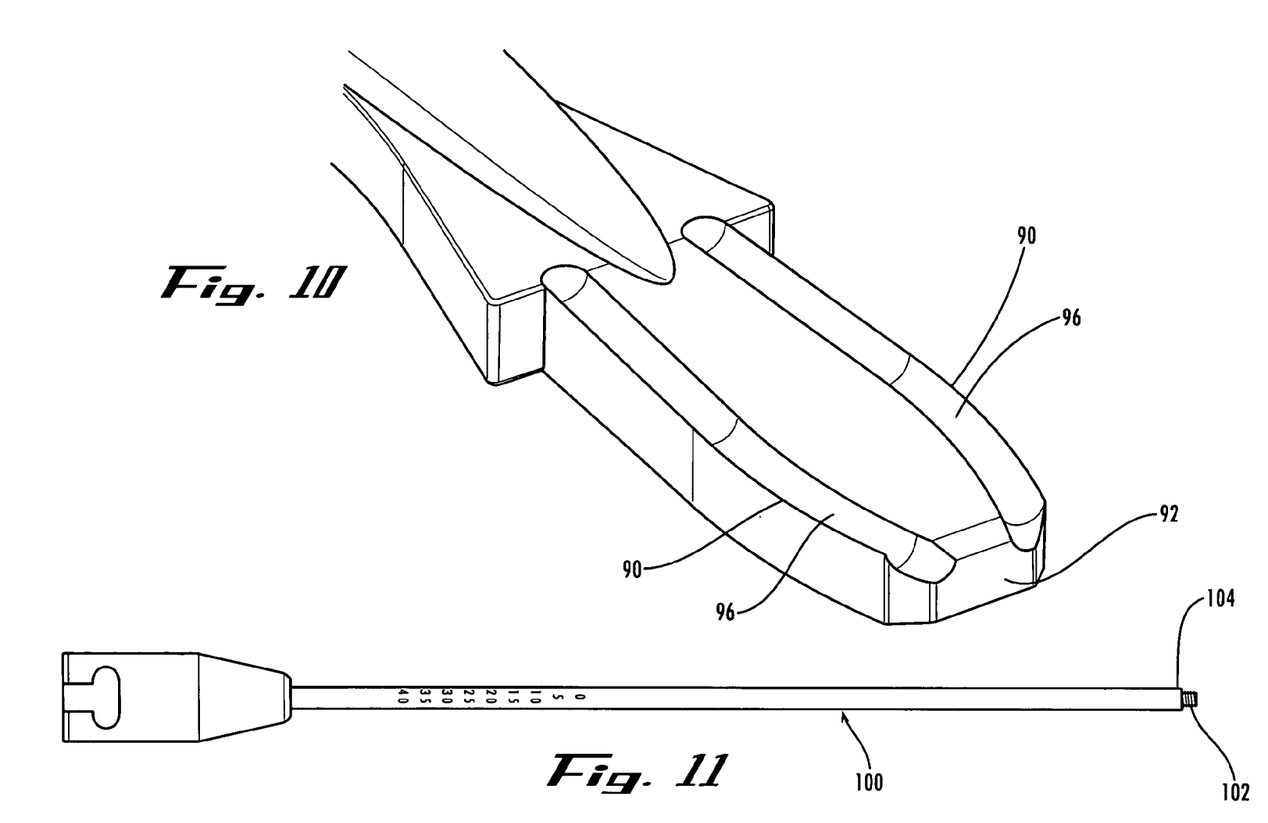
FIG. 10 is a perspective view of an alternative embodiment of a monorail instrument of this invention.
FIG. 11 is a side view of an insertion tool of this invention.
Figure 11:
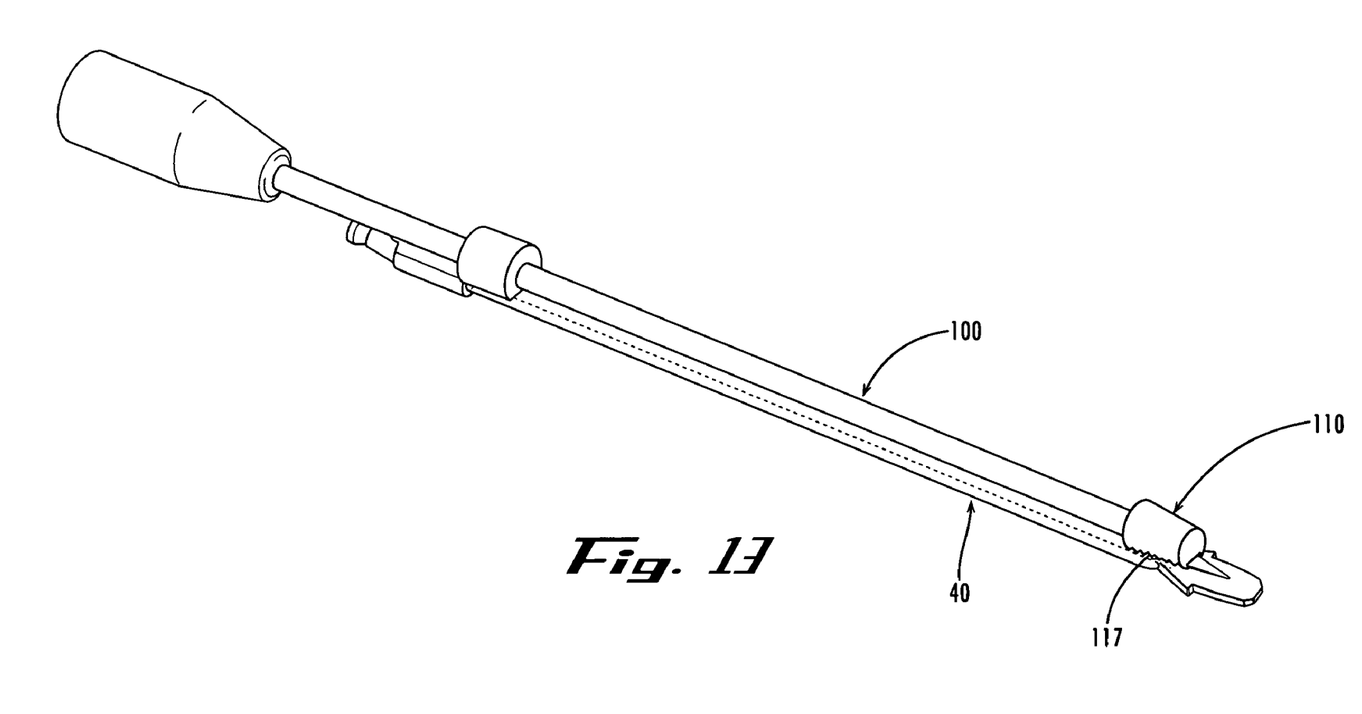
Figure 14:
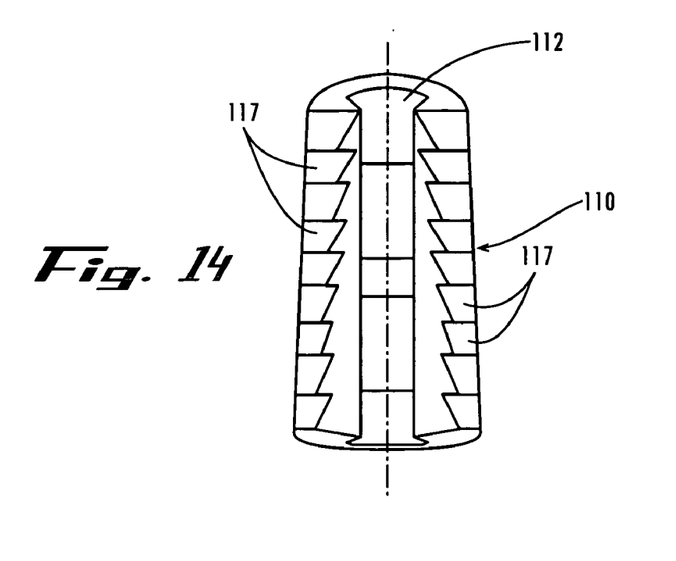
FIGS. 14-16 are alternative side views of an implant of this invention.

Once the disc space is prepared and ready for fusion, an inserter, shown in FIGS. 11 and 12, is used to place an implant, shown in FIGS. 13-16, into the disc space. Inserter 100 includes threads 102 on leading end 104, which engage threaded aperture 106 on implant 110. The implant 110 includes channel 112, shown in FIG. 14 and similar to channel 72 of chisel 70 described above. Channel 112 of implant 110 engages monorail 44 of distractor 40 so that inserter 100 and implant 110 slide down distractor 40 and into the disc space. In one embodiment, a guide 111, shown in FIG. 12, may be used to maintain the engagement of the inserter 100 with the monorail 44.

Figure 15:
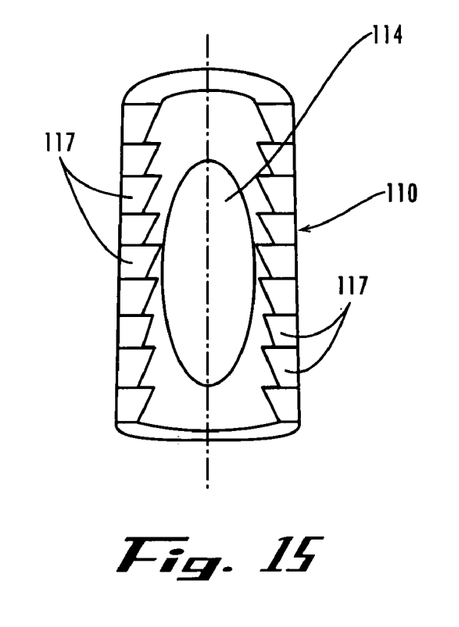
Figure 16:
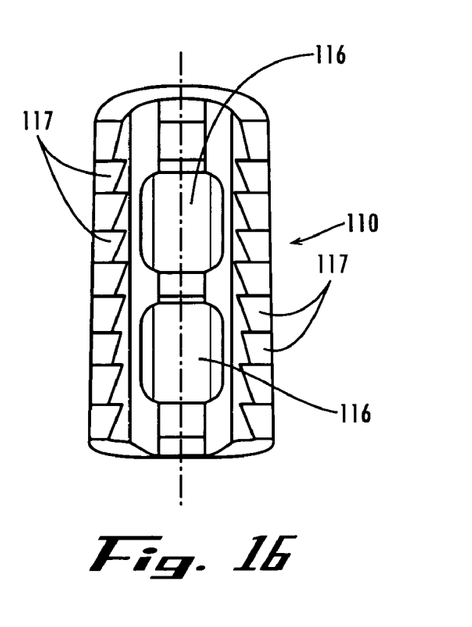

Once implanted, openings on implant 110, such as oval apertures 114 and additional apertures 116, shown in FIGS. 15-16, allow bone to grow through the implant and stabilize the fusion of the two vertebrae. As shown in the drawings, the channel 112 of the implant 110 is located on the inner wall of the implant 110. Two implants can thereby be nested together to provide a better anatomical fit to the interbody space and reduce the chance of neural injury to the lateral or descending nerve roots. The implant has raised teeth 117 to help prevent retropulsion once delivered to the disc space.

In an alternative embodiment, a delivery system of this invention includes a distractor having a channel for accepting a monorail. In this embodiment, the implant includes a monorail. Additional instrumentation, such as a chisel and a rasp, may also be designed to include a monorail, so that these instruments engage the channel of the distractor.

Figure 17:
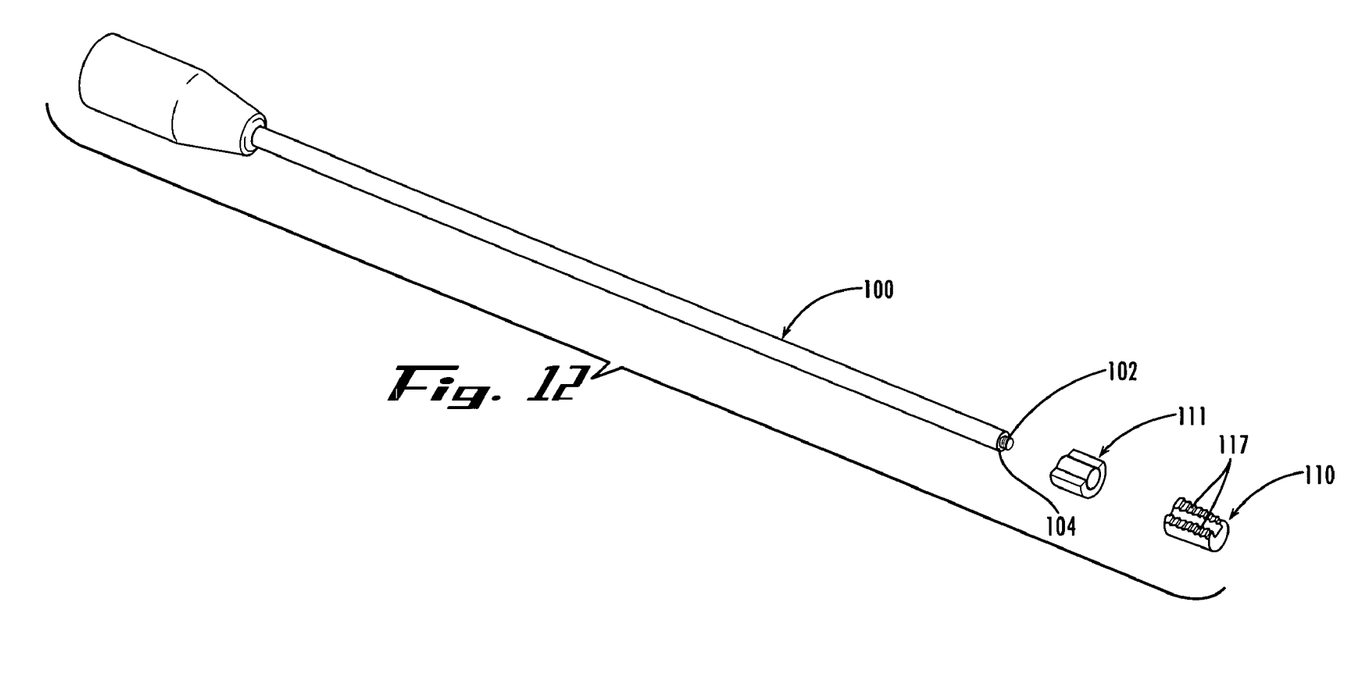
FIGS. 17-18 are perspective views of alternative embodiments of this invention.
Figure 18:
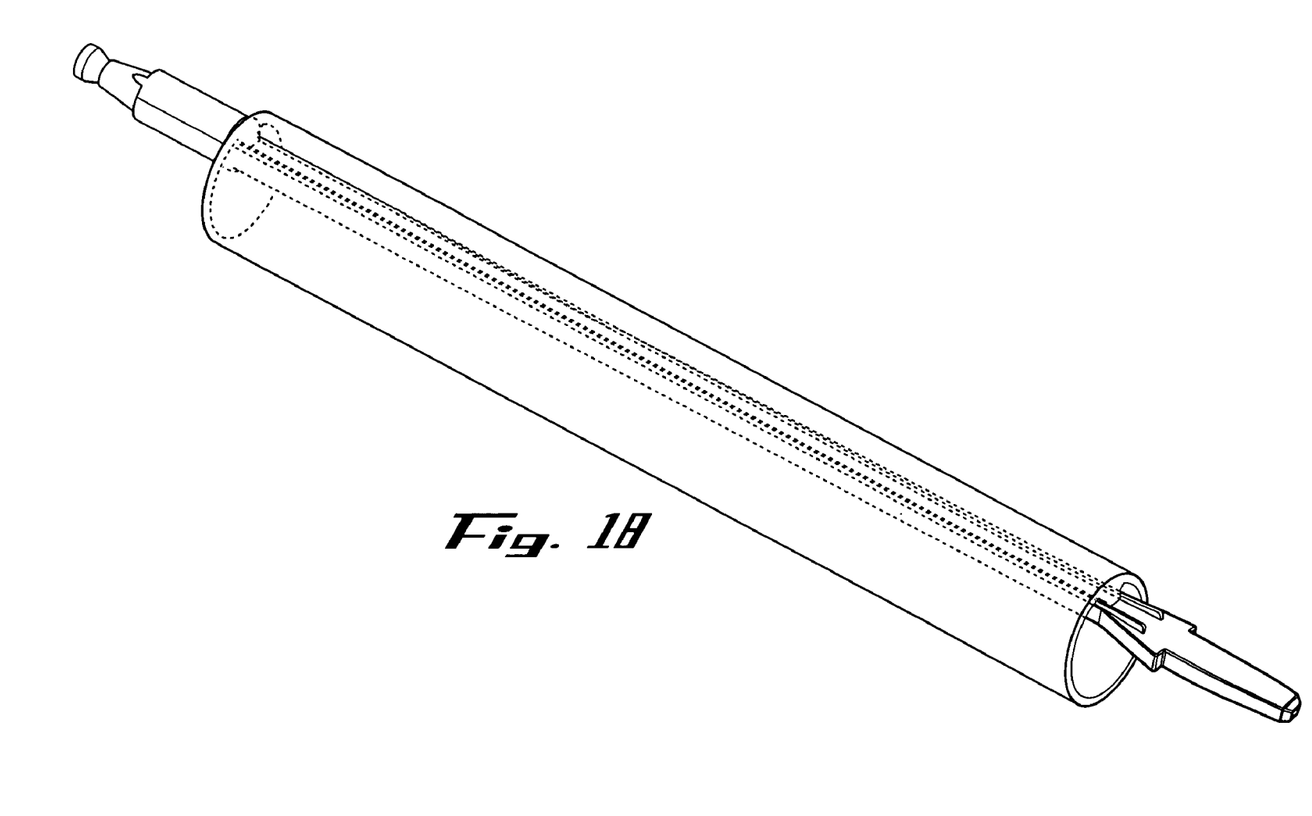

Embodiments of this invention may be used with standard instrumentation, as well as through a channel or circular delivery system that is introduced by a collapsed tubular retractor that is inserted into the surgical site and dilated. In one embodiment, shown in FIG. 17, a tubular retractor includes a monorail, so that an implant having a channel engages the monorail and slides down the tubular retractor into the disc space. In another embodiment, shown in FIG. 18, the tubular retractor includes a channel adapted to engage a monorail, so that an implant having a monorail engages the channel and slides down the tubular retractor into the disc space.

The monorail distractor 40 of this invention may be made in various sizes to accommodate different patient anatomies. In one embodiment, a 7 mm distractor is used. In other embodiments, the distractor is 9, 11 or 13 mm distractor, or any other suitable size.

Figure 19:
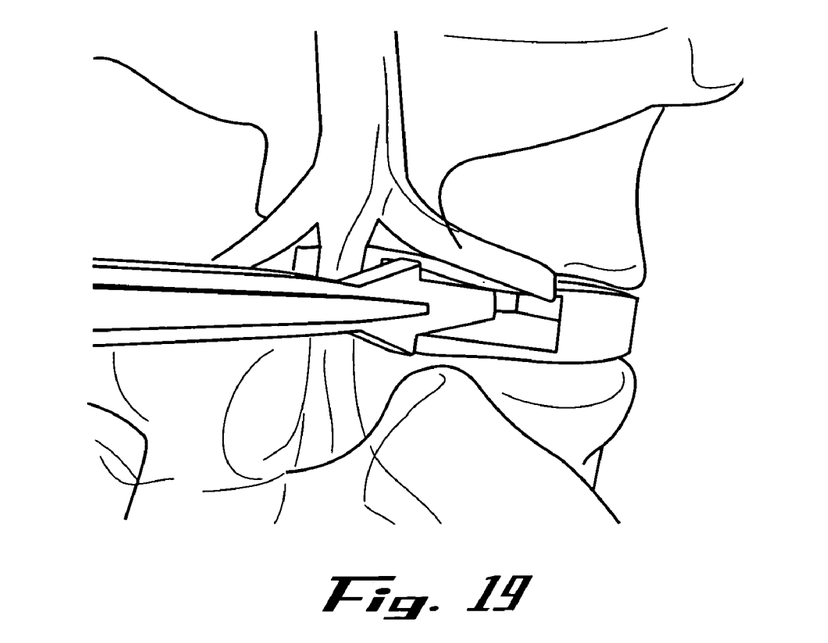
FIG. 19 illustrates placement of a monorail tool of this invention into the intervertebral space.
Figure 20:
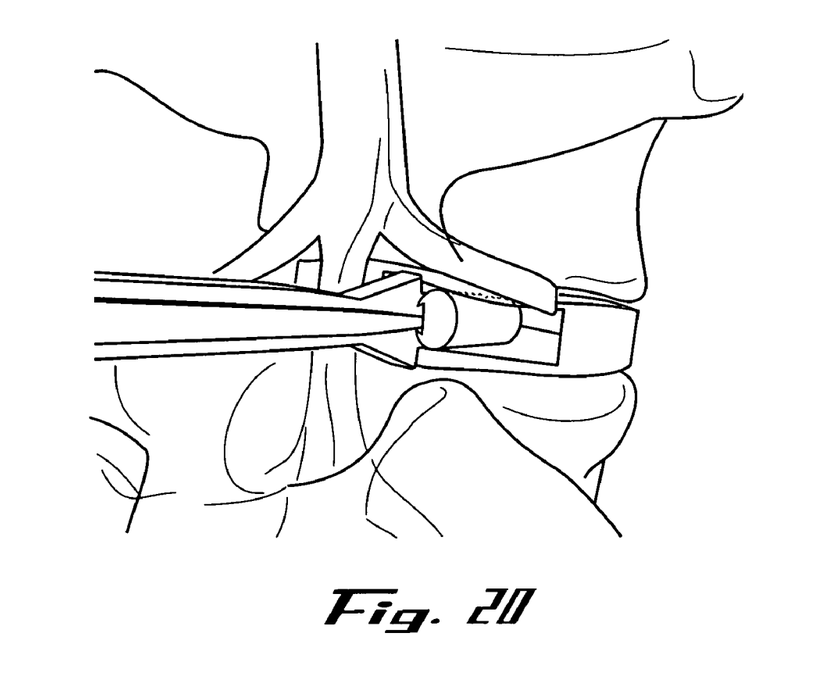
FIG. 20 illustrates placement of an implant of this invention into the intervertebral space.

FIGS. 19-20 illustrate placement of a monorail distractor (FIG. 19) and an implant (FIG. 20) according to this invention.

While this invention has been described in detail with particular reference to the disclosed embodiments, it will be understood that variations and modifications can be affected within the spirit and scope of the invention as described herein and as defined in the appended claims.

The invention claimed is:

1. A method of performing a spinal fusion procedure, comprising:
   (a) inserting a distractor into the disc space of a patient, the distractor having a monorail on a lateral side, the monorail comprising a single, elongated member;
   (b) rotating the distractor 90 degrees to distract the disc space;
   (c) engaging a channel of a disc space preparation instrument with the single, elongated member of the monorail of the distractor so that the disc preparation instrument and the distractor are slidable relative to one another in a longitudinal direction, but not in a lateral direction;
   (d) sliding the disc space preparation instrument down the monorail and into the disc space;
   (e) cleaning and preparing the disc space using the disc space preparation instrument;
   (f) removing the disc space preparation instrument;
   (g) threading an implant to an insertion tool having a channel;
   (h) joining the insertion tool with the monorail of the distractor; and
   (i) pushing the implant down the monorail of the distractor and into the disc space using the insertion tool.

2. The method of claim 1, wherein the step of joining the insertion tool with the monorail of the distractor comprises:
   engaging the channel of the insertion tool with the single, elongated member of the monorail of the distractor so that the insertion tool and the distractor are slidable relative to one another in a longitudinal direction, but not in a lateral direction.

3. The method of claim 1, further comprising:
   (j) disengaging the implant from the insertion tool; and
   (k) removing the insertion tool and the distractor instrument from the disc space.

4. The method of claim 1, wherein the disc preparation instrument is a chisel.

5. A method of performing a spinal fusion procedure, comprising:
   (a) inserting a distractor into the disc space of a patient, the distractor having a monorail on a lateral side, the monorail comprising a single, elongated member;
   (b) rotating the distractor 90 degrees to distract the disc space;
   (c) engaging a channel of a disc space preparation instrument with the single, elongated member of the monorail of the distractor so that the disc preparation instrument and the distractor are slidable relative to one another in a longitudinal direction, but not in a lateral direction;
   (d) sliding the disc space preparation instrument down the monorail and into the disc space;
   (e) cleaning and preparing the disc space using the disc space preparation instrument;
   (f) removing the disc space preparation instrument;
   (g) threading an implant having a channel to an insertion tool;
   (h) joining the implant with the monorail of the distractor; and
   (i) pushing the implant down the monorail of the distractor and into the disc space using the insertion tool.

6. The method of claim 5, wherein the step of joining the implant with the monorail of the distractor comprises:
   engaging the channel of the implant with the single, elongated member of the monorail of the distractor so that the implant and the distractor are slidable relative to one another in a longitudinal direction, but not in a lateral direction.

7. The method of claim 5, further comprising:
   (j) disengaging the implant from the insertion tool; and
   (k) removing the insertion tool and the distractor instrument from the disc space.

8. The method of claim 5, wherein the disc preparation instrument is a chisel.

* * * * *

UNITED STATES PATENT AND TRADEMARK OFFICE
CERTIFICATE OF CORRECTION

PATENT NO. : 7,615,079 B2
APPLICATION NO. : 11/407585
DATED : November 10, 2009
INVENTOR(S) : Flickinger et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (471) days Delete the phrase "by 471 days" and insert -- by 675 days --

Signed and Sealed this

Eighteenth Day of May, 2010

David J. Kappos
*Director of the United States Patent and Trademark Office*